United States Patent [19]

Fertig et al.

[11] Patent Number: 4,806,314
[45] Date of Patent: Feb. 21, 1989

[54] ORGANIC FLUID DETECTION SYSTEM AND APPARATUS

[75] Inventors: Glenn H. Fertig, Natrona Heights; T. Lee Zinn, Zelienople, both of Pa.

[73] Assignee: Mine Safety Appliance Company, Pittsburgh, Pa.

[21] Appl. No.: 3,944

[22] Filed: Jan. 16, 1987

[51] Int. Cl.[4] .................................... G01N 27/12
[52] U.S. Cl. ............................. 422/78; 422/90; 422/95; 422/98; 436/149; 436/152; 73/27 R
[58] Field of Search ............... 73/23, 27 R; 422/68, 422/78, 81, 83, 90, 95, 96, 98; 436/52, 149–152

[56] References Cited

U.S. PATENT DOCUMENTS

| 2,618,150 | 11/1952 | Willenborg | 422/96 X |
| 2,652,315 | 9/1953 | McEvoy | 422/96 |
| 4,201,088 | 5/1980 | Trietley, Jr. | 374/114 |
| 4,414,839 | 11/1983 | Dilley et al. | 422/98 X |
| 4,443,791 | 4/1984 | Risgin | 422/98 X |

*Primary Examiner*—Barry S. Richman
*Assistant Examiner*—Jill Johnston
*Attorney, Agent, or Firm*—Reed, Smith, Shaw & McClay

[57] ABSTRACT

An organic fluid detection instrument having great sensitivity to low concentrations or organic fluids in a fluid stream comprise a conduit adapted for the one-way flow therethrough a mixture of an oxygen-containing carrier fluid and organic fluids; a first electrical resistance element disposed in the conduit and carrying a material catalyst for promoting exothermic oxidation reactions of the organic fluid of the mixture; a second resistance element also disposed in the conduit for temperature sensing, consisting of a material with an electrical resistivity that varies with its induced temperature; each element is connected to a pair of electrical leads for operatively producing electrical signals representative of the amplitude of the output signal to be measured; a measuring circuit means is joined to both pairs of leads for processing both a synchronous signal and the second output signal in a manner whereby variations in the differential resistance of the second sensing element serve as a measure of the concentation of the entrained fluids in the entering fluid mixture.

12 Claims, 2 Drawing Sheets

ORGANIC FLUID DETECTION SYSTEM AND APPARATUS

FIELD OF THE INVENTION

The invention relates to detecting the presence of relatively low concentrations of organic fluids present in air mixtures. In another aspect, it relates to a detection instrument for detecting and measuring hydrocarbons present at low levels and flowing fluid streams.

BACKGROUND OF THE INVENTION

In certain industrial settings, the presence of organic fluids that are combustible gases, such as alkanes, like methane or hydrogen, may reflect leakages in piping systems, would constitute a fire and explosion hazard if permitted to accumulate undetected. Another high-risk environment is methane in the air of underground mine shafts. Precautions are needed to protect from such hazards by continuously or sporadically monitoring flowing fluid streams to preclude hydrocarbon concentrations from reaching a dangerous level.

In other commercial applications, there is a need to monitor the exhaust solvent (organic) fluids from such sources as paint and varnish applications, chemical processes and internal combustion engine exhausts, all of which may be expended to the atmosphere. Moreover, recent governmental action through more stringent air pollution control laws, are intended to limit the admission of organics, and perhaps carcinogenic organic chemicals into the atmosphere. The growing need for detection and remedial steps is thus well documented.

Available organic fluid detectors may conventionally utilize a detector filament or catalytic detector elements, elements which may be electrically heated to provide for oxidation at the filament surface of the organic components. Such catalytic elements may be included in a detection circuit, such as a Wheatstone bridge circuit, containing a reference element which does not provide for a reaction of the organic fluid at the reference element surface. The resistance of such a catalytic element is a function of the temperature of the element, and when the filament resistance is increased by the heat of reaction of the organic fluid, the presence of the organic fluid may be detected by its differential effect on the catalytic element in respect to the reference element. There has been a long standing need for providing a low cost, high sensitivity organic fluid concentration detector, typically for use around organic fluid storage facilities.

The prior art methods work for high concentrations of organic fluids, but when it becomes necessary to strain the sensitivity of such devices to detect low concentrations (ranging from five percent downwardly), the prior art methods, evidence a lack of stability. This may apparently be caused by electrical noise in the detector, and long-term drifting of the fluid concentration indicator. This may also be caused by short-term electrical noise and long-term resistance changes in the detector element.

Early attempts were made to improve stability by adding a compensating filament. A similar filament to that of the fluid detector filament was placed on an adjacent arm of a Wheatstone bridge circuit. Changes in ambient temperature and power supply voltage produce similar changes in the two filaments, but their location in the circuit is such as to produce oppositely acting responses in the output signal. The circuit is therefore stabilized against changes that affect the two filaments equally. Oxidation of the organic fluid sample to be analyzed is prevented by not exposing the compensator filament to the organic fluid sample or by operating it at a lower temperature. Instruments of this type are described in U.S. Patents to R. E. Hartline, Combustible Gas Indicator, 2,279,397; and M. G. Jacobson, Combustible Gas Indicator, 2,244,366. These detection schemes work well when the organic fluid concentration is high. (5% methane in air, or more, full scale). A critical deficiency is that their stability decreased as the full scale sensitivity increased.

In the more recent past, attempts have been made to solve this chronic shortfall. For example, Hartline invented an organic fluid detector system based on the use of thermal hysteresis (U.S. Pat. No. 2,617,716). While he was successful in detecting high fluid concentrations with great zero stability, the device failed to have the necessary sensitivity to detect low levels of organic fluids.

Systems have been proposed for keeping of the sensing element at ependable levels in the face of widely varying organic fluid concentrations. However, they have practical disadvantages, so improved detectors for low organic fluid detection and measurement are still to be sought.

OBJECTS OF THE INVENTION

It is therefore an object of the present invention to provide a fluid detection apparatus which can detect with reliable accuracy organic fluid components in mixtures without being disabled by the occurrence of low concentration levels. It is a further object of the invention to provide an organic fluid detection apparatus which can be readily and economically fabricated. It is another object of the invention to provide a system for measuring a low hydrocarbon contaminant content in an airstream from industrial sources by utilizing a facile and economic fluid detector. It is another object of the invention to provide a fluid measurement circuit which bypasses the long used, and somewhat more costly, Wheatstone bridge circuit. A still further object of the invention is to provide an organic fluid detection system adapted for providing a substantially linear measurement response to varying fluid organic fluid concentrations down to comparatively low levels.

These and other objects of the present invention will become apparent from the following detailed description and the accompanying drawings, of which:

SUMMARY OF THE INVENTION

Figure 1:
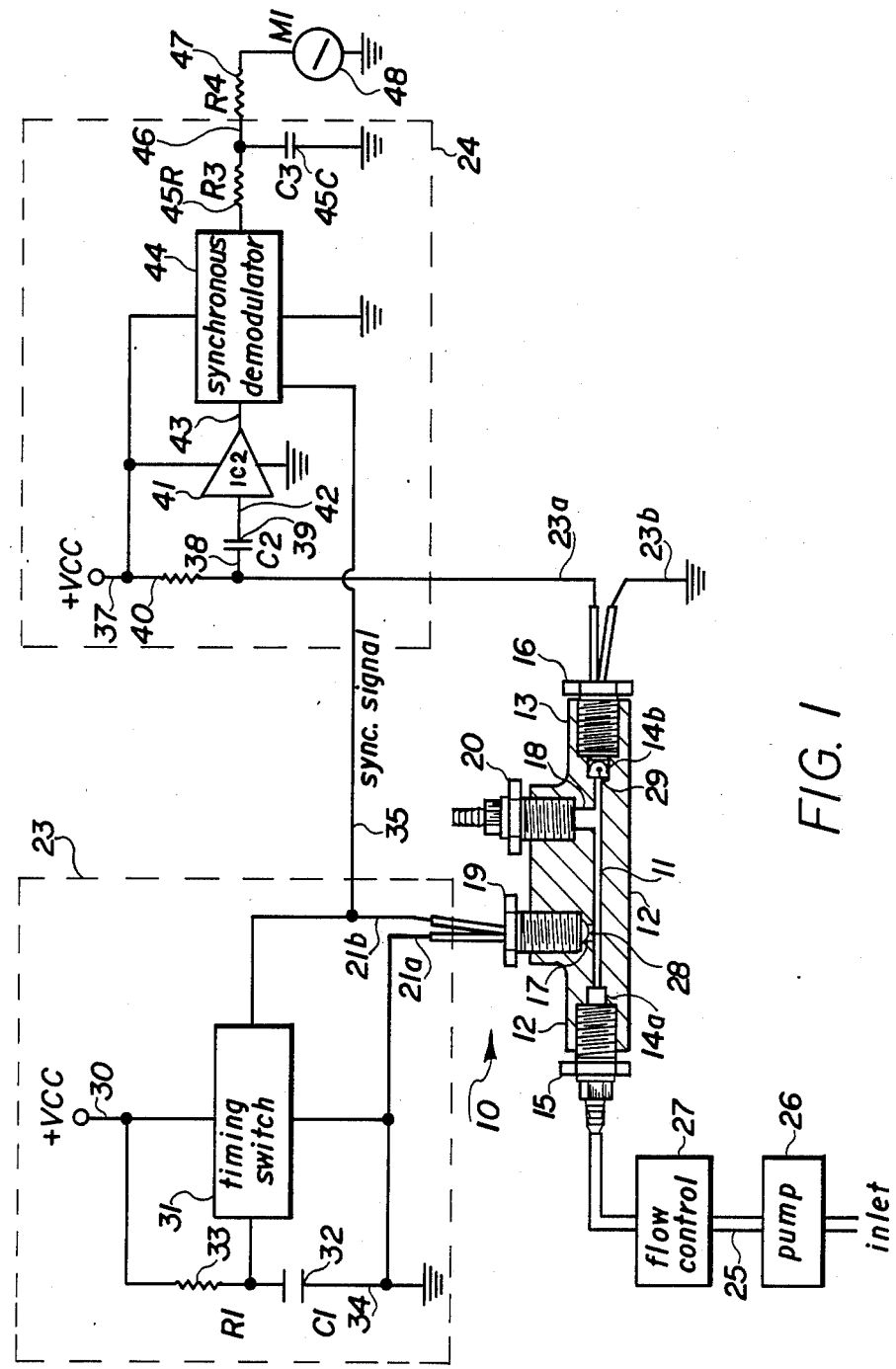
FIG. 1 is a combined circuit diagram and schematic view, partially in section, of a preferred embodiment of the invention illustrating the circuit components thereof and the manner of their interconnection.

The system of the present invention obviates the foregoing limits of the described prior art, in having high, full-scale sensitivity, e.g., 1000 p.p.m. of methane in air, or lower, which is obtained with long-term zero stability, plus or minus 1% over months of use. According to one aspect of the present invention, there is provided an organic fluid component detection apparatus comprising first and second fluid sensing elements, with both elements including a metal which exhibits variable electric resistance, depending upon the temperature of the fluideous components to be detected, and with each element bearing a catalyst for promoting oxidation reactions of the organic fluids; the second element is spaced apart from and downstream of the first element and comprises a metal filament which acts as both a heater and a resistance element that varies with the temperature induced in it; a first and second pairs of electrical leads are operatively connected to each of the sensing elements, for permitting resistance heating, and for the second pair to serve to reflect variations in electric conductivity exhibited at the second element, as its temperature varies in response to the sensible heat produced by the oxidation of the organic fluids; a pair of voltage control circuits are coupled to each of the sensing elements, serving to controllably heat the elements, and to cause controlled but substantial oxidation of the organic fluids passing thereby; and a measuring circuit is adapted to be operatively joined to the second pair of electrical leads for producing an alternating output signal, which signal is proportional to the concentration of the organic fluids in the mixture entering the detection apparatus. A typical fluid stream for analysis will be an oxygen-containing carrier fluid with up to a few percent of a hydrocarbon, like methane.

According to a preferred embodiment of the invention, the first and second elements each carries a catalyst for promoting further oxidation reactions of the uncombusted fluids to be detected, and the second output signal resulting from the second element response is then AC-coupled through a capacitor means and a resistor means, both serving as a high bandpass first filter, for producing a modified AC third output signal. The third signal is then passed to a combined amplifier, demodulator and second filter, serving to make it suitable for presentation on metering means or other display means. The display signal is quantitatively correlatable with the concentration of the organic fluids in the entry fluid mixture.

In another embodiment, the disclosed device can be adapted to any fluid analyses where a flowing fluid sample contains an entrained fluid adaptable to a change in its molecular structure, like a modifiable chemical composition, by a means that can be alternately turned on and off, as is the case with the first fluid sensing element of the first embodiment. A typical fluid stream for this approach would be an air stream containing low concentrations of either halogenated organics (FREON ® fluids), or nitrogenated organics, which are then subjected to intermittent heating at the first element. The changes in their compositions are detected by an amperometric cell (known in the art), serving in place of the downstream resistance and sensing elements, outlined above as to the first embodiment.

DETAILED DESCRIPTION OF THE INVENTION

Turning now to the drawings, the present invention in its various aspects will be more precisely described with respect to the embodiments therein depicted.

Referring to the drawings, and to FIG. 1 in particular, the detector 10 comprises a longitudinal bored conduit 11, preferably cylindrical, which is located in a solid body 12. Both of the opposing conduit ends 12 and 13 have countersinks, 14a and 14b. The ends are also tapped to admit a pipe coupling 15 and/or a bushing 16 for electrical leads. The intermediate segment of detector 10 has two spaced apart and larger boreholes, 17 and 18, both also being tapped, and conveniently being vertically positioned as shown in the embodiment depicted. Each of the larger bores is also provided with a adapter plug, 19 and 20, respectively. The left side adapter plug 19 is a hermetically-sealed bushing, adapted to serve as a conduit for a pair of electrical leads, 21a and 21b, which operatively connect to a circuit 23, the function of which is to be described.

The right side adapter 20 is a pipe coupling, with an optional outer nipple, which serves as the outlet for the vented combusted and carrer fluids.

Hermetically-sealed bushing 16 is at the rightmost end of the detector. It provides a second conduit for a second pair of electrical leads 23a and 23b, leading to an output signal processing circuit 24, to be described.

The leftmost end coupling 15 serves to admit an organic fluid mixture into the detector body.

The fluid enters via a conduit 25, having a pump means 26, and a flow controller device 27, sequentially positioned therein, with both being upstream of the detector entry point 12.

Detector 10 is in the nature of a solid body. The main bore 11, for example, is about 0.0625 inches in diameter, and about four inches in length with the described substantially larger countersinks, to accommodate the adapters. Their fabrication is well known as within the skill of the relevant art.

Operatively, the detector 10 consists of a first resistance element 28 and a spaced apart, second resistance (also sensor) element 29. Element 29 is located downstream of element 14, typically about 2 inches away. The optimum spacing of the two resistance elements is a function of the fluid mixture flow rate, and can be set empirically for the character of the fluid stream being measured.

Upstream element 28 is of a dual nature, conventionally being fabricated of a resistance heating member (for example, platinum wire) and covered by a catalytic coating of a metal, like palladium, which catalyzes oxidation of the hydrocarbon fluids. Element 28 is electrically connected via leads 21(a) and 21(b) to a controlled DC voltage source 30. It is also provided with a timer switch 31, such as 555 timer (31) of the Motorola IC Data Book 1986, both being positioned within a first control circuit 22. This first circuit serves to intermittently heat the first element for a predetermined period, so as to foster substantial oxidation of the passing fluid, typically by resistance heating for ten seconds, or so. Preferably, the on-off times are made of equal duration. Capacitor 32 and a resistor 33, located in leg 34 of circuit 22, produce a voltage time constant serving to produce an AC signal on the upstream resistance element 28. A synchronous signal passes from circuit 22 to circuit 24 via lead 35.

The heating time itself is to be set as a function of the mass of the filament itself, the thermal conductivity of the organic fluid and the fluid flow rate. Thus, it will be determined empirically for the specific fluid mixture and flow rate(s) to be tested for its hydrocarbon concentration.

Downstream element 29 is of a dual construction and a dual function, as well. Conveniently, it is formed of a metal adapted to serve primarily as a resistance heating element, like platinum, but it is also provided with a catalytic coating thereon to oxidize the rest of the unburned organic fluids.

The second voltage control circuit 24 is connected via a pair of leads in 23(a) and 23(b) to resistance/sensing element 29 to a DC voltage source 37, which is employed for inducing the electrical heating of the element 29. This element is to be maintained at a preset temperature during the flowby of the fluid mixture. Also, element 29 acts to sense variations in the metallic element's resistance, which are induced by the varying temperatures of the flowing organic fluids, that are being intermittently partially combusted at the first element 28. As the remaining fluid combusts, the ambient temperature at element 29 increases and its resistance changes. In the case where platinum is the sensor metal of element 29, the resistance increases with rising temperature producing a signal. This varying AC output signal is approximately proportional to the entry fluid stream organics concentration.

The output signal 23a goes via a lead 38 to be AC-coupled with a capacitor 39. Capacitor 39 and the input resistance of the amplifier 41 function as a form of a high pass filter. This filter function improves the long-term stability of the detector. Amplifier 41, for instance an Amplifier (41) Type INA104 found in Burr Brown Data Book 1986, serves to amplify, detect and filter a partly processed input signal 42.

In a preferred embodiment, the filtered and amplified output signal 43 preferably passes to a synchronous demodulator 44 serving as a lock-in amplifier. Lock-in amplification is employed to separate the relatively low amplitude signal 43 from interfering noise. Modulator 44, such as a Synchronous Demodulator (44) Type Ad630 as described in Analog Device Corp. Data Book 1986, thus acts as a combined signal detector and narrow band filter and provides an enhanced sensitivity for the detection system. However, a non-synchronous demodulator can be used for the detection of the signal, as well.

Consequently, with the present invention, very small signals can be detected in the presence of large amounts of random noise, provided that the frequency and phase of the desired signal are known.

The described lock-in amplification means is essentially the demodulator 44, followed by a low-pass filter, comprising resistor 45R and capacitor 45C. The small signal's frequency and phase are determined by the synchronous signal coming by a lead 35 from circuit 22.

The separated and refined signal, which is representative of the initial concentration of organic fluid entering detector 10, then passes via lead 46 through a permanent resistor 47 for readout, typically on a display meter 48.

In the operation of the invention, an organic fluid enters the detector 10 through the longitudinal bored conduit 11. The organic fluid flow into the conduit 11 is maintained at a constant rate by flow control device 27. As the organic fluid proceeds down the conduit 11, the first resistance element 28, which has a current passing therethrough from circuit 22, catalyzes oxidation of the organic fluid.

At a point downstream of the resistor 28 essentially all the organic fluid has been removed due to oxidation by resistor 28. Downstream resistance element 29 oxidizes any remaining unburned organic fluid, and in so doing, senses the noise level present in the conduit 11. This is accomplished by resistor 40 and downstream element 29 being in series, with element 29's resistance being a linear function of it's temperature. Since most of the organic fluid is oxidized by element 28, only stray heat or noise is present to heat element 29. The resistance associated with this noise added with the fixed resistance of resistor 40 corresponds to a base or reference level.

After approximately ten seconds, timing circuit 22 stops current flow to resistor 28 and at the same time sends a synchronized signal along lead 35 to activate the synchronous modulator 44 of circuit 24. The organic fluid now passes resistance element 28 in an unchanged form since there is no current to the resistor and thus no oxidation. Oxidation of the fluid instead occurs at downstream element 29. When oxidation occurs at downstream element 29, the heat produced from the oxidation of the organic fluid increases the resistance of downstream element 29 in an amount proportional to the amount of organic fluid present. It should be noted that the heat from the oxidation of all the organic fluid around downstream element 29 is in addition to the already present heat noise that downstream element 29 has sensed when resistance element 28 was oxidizing the organic fluid.

The series resistance of resistor 40 and resistor 29 by changing over time with a frequency corresponding to the frequency of timing circuit 22, provides an AC component to the DC current that is flowing out of the voltage source 37. The capacitor 39 that is connected to lead 23a by lead 38 removes the DC component of the current and allows only the AC component to pass. This AC component, which has its highest value corresponding to the concentration of organic fluid being sampled and its lowest value corresponding to the noise level, passes from capacitor 39 along lead 42 to amplifier 41 to improve the strength of the signal. This amplified signal passes along lead 43 to synchronous modulator 44 which essentially rectifies that part of the signal passing along lead 43 which is attributable to the oxidation of the organic fluid and the noise. The signal emerging from the synchronous modulator 44 passes along to resistor 45R and capacitor 45C, and to resistor 47 and display meter 48. Resistor 45R and capacitor 45C form a low pass filter which prepares the signal for display by display meter 48.

Additionally, timing circuit 22 is powered by voltage source 30. Resistor 33 and capacitor 32 form an RC timing circuit which drives timer switch 31. Timing switch 31 in turn controls when current flows to resistor 28 and when a synchronous signal is sent along lead 35 to the demodulator 44.

Experimentally, it was determined that an organic fluid flow rate for the aforedescribed detector would be within the range of 5 to 25 cc/per minute, depending on the exact detector dimensions. It was found that a fluid flow rate of about 17 cc per minute was an optimum one for low organic levels determinations. It was also determined that if downstream sensor element 29 is positioned so as to let the combusted fluid flow impinge directly upon it, (as is depicted), then the largest amplitude measurement signal is obtained.

To determine the optimum operating conditions of the fluid detector, shown in the drawing, the following tests were conducted and their results recorded. Two different fluids were tested, methane and propane, with the gross flow rates being adjusted with flow controller 27, from 4 to 750 cc/minute. At each different flow rate, the peak-to-peak voltage output was recorded at the output 23a to 23b of the fluid sensor device 10.

The calibration of the detector device 10 is within the skill of the art for any state-of-the-art fluid detector.

First, the optimum operating conditions of the detecting device must be assessed. In our device, the temperature of the first catalytic bed 28 must change from at least 600° C. (as pointed out by Hartline in U.S. Pat. No. 2,279,397) to less than the temperature that will support combustion of the organic fluids fluid understudy interest.

Next, the fluid flow must be adjusted to an optimum rate. This point was determined empirically in the data given in Table I. However, one should note from the data, that the optimum flow rate is different for each organic fluid.

Finally, the calibration of the detector is accomplished by flowing a carrier fluid, free of any organics, into the detector via conduit 25, (in this example, organics-free air) and then to insure the visual meter 48 goes to zero.

After establishing the zero, a span fluid is flowed into the detector via the inlet conduit 25. For example, 1% Methane in air. The gain of the second electronic control circuit 24 is adjusted, until the reading of meter 48 is at the desired value. In this case, the meter 48 is 100% of its full scale. In our device, the preferred gain adjustment is accomplished by adjusting the gain of amplifier 41 of circuit 24.

If it is desired to obtain higher sensitivity, such as 1000 or 100 parts per million of organics, or higher, then a span fluid of the appropriate value should be used and the gain of the system adjusted accordingly.

After the device 10 is calibrated, the meter 48 will indicate concentrations directly, in percent of full scale for the organic fluid placed in the detector. Thus, if the detector was calibrated for 1% Methane in Air, or full scale, and when room air was flowed through the detector, the meter 48 read 26% of full scale. Then the concentration of methane in the room air would be 26% of 1%, or 0.0026% methane in air.

Figure 2:
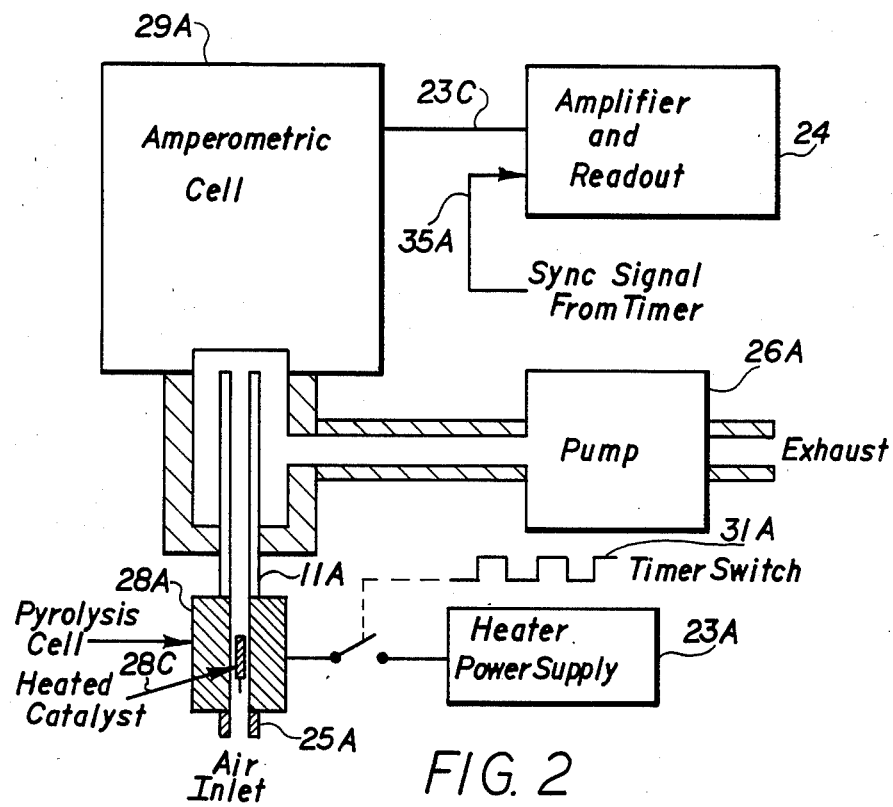
FIG. 2 is a schematic diagram of an alternate measurement system for dissimilar types of chemical compounds in flowing fluid streams.

In FIG. 2 is seen a schematic view of the circuitry and associated components which have been modified to process and detect low-level concentrations of diatonic compounds like organic compounds, not characterized by suitability for change in molecular structure, such as FREON ® fluids.

The modified carrier fluid enters via conduit 25A to flow through a pyrolysis cell 28A, in which is suspended a catalyst material 28C, that will effect at least a partial degradation of the entrained organic compound. An AC voltage source 23A provides for heating of cell 28A by use of a time switch 31A, being operated cyclically in the manner described for the first embodiment. The partly pyrolyzed organics flow via conduit 1A to impinge on an amperometric cell 29A (See, "A New Portable Monitor for Halogenated and Nitrogenated Organics in Air", C. W. Gardner, North Coast Conference for Instrument Society of America, Cleveland, Ohio, 1986), which serves, as did the sensing cell 29 of the first embodiment, to sense variations in amperage induced by the flow fluid temperature changes. The output signal 23C from the modified detection cell 29A is processed electrically (and displayed) essentially identical to the manner described for the first embodiment.

TABLE 1

EFFECT OF FLUID MIXTURE FLUID FLOW RATES ON MEASURED ELECTRICAL SIGNALS

| Flow cc/Min | Signal in Millivolts (MV) Peak-to-Peak | Current in Milliamperes (MA) Element 28 | Current in Milliamperes (MA) Element 29 |
|---|---|---|---|
| A. 1% Methane in Air | | | |
| 6 | 2.1 | 450 | 360 |
| 8 | 2.2 | 450 | 360 |
| 20 | 5.1 | 450 | 360 |
| 25 | 4.9 | 450 | 360 |
| 82 | 4.3 | 450 | 360 |
| 240 | 2.0 | 450 | 360 |
| B. 1% Propane in Air | | | |
| 4 | 4.2 | 450 | 360 |
| 8 | 4.2 | 450 | 360 |
| 14.5 | 4.3 | 450 | 360 |
| 15.5 | 4.3 | 450 | 350 |
| 23.0 | 4.1 | 450 | 350 |
| 43.0 | 3.6 | 450 | 350 |
| 750.0 | 1.7 | 450 | 350 |

What is claimed:

1. An entrained fluid detection instrument having great sensitivity to low concentrations of diatomic compound fluids in a fluid stream comprising:
    (a) first conduit means adapted for the one-way flow therethrough of a mixture of a carrier fluid and an entrained diatomic fluid;
    (b) a first reaction element disposed in a portion of the said first conduit means supporting a material for promoting reactions of the entrained fluid of the mixture;
    (c) a first sensing element also disposed in the first conduit means for detecting ambient changes in said first conduit and spaced apart from said first reaction element, comprising a material with an electrical resistivity that varies with its induced temperature, said first sensing element electrically isolated from said first reaction element;
    (d) a first pair of electrical leads operatively connected to said first reaction element;
    (e) a first AC voltage power circuit coupled to the first pair of leads and operable to intermittently heat the first reaction element sufficient to cause substantial degradation of organic compound fluids in the entrained fluid of the mixture Passing by said first reaction element, and to produce a synchronous signal;
    (f) a second pair of electrical leads operatively connected to said first sensing element for sensing variations in the electrical resistance thereof caused by temperature changes occurring in said first sensing element, said electrical resistance thereof represented by a second output electrical signal; and
    (g) measuring circuit means adapted to be operatively joined to said first and said second pairs of leads being activated by and for processing the synchronous signal and the second output signal respectively, whereby variations in the differential resistance of the first sensing element serve as a measure of the concentration of organic compound fluids in the fluid of the mixture.

2. An organic fluid detection instrument having great sensitivity to low concentrations of organic fluids in a fluid stream comprising:
    (a) first conduit means adapted for the one-way flow therethrough of a mixture of an oxygen-containing carrier fluid and organic fluids:

(b) a first electrical resistance element disposed in a portion of the said first conduit means and supporting a catalytic material for promoting exothermic oxidation reactions of the organic fluid of the mixture;

(c) a second electrical resistance element also disposed in the first conduit means for temperature sensing, spaced apart rom said first resistance element, comprising a material with an electrical resistivity that varies with its induced temperature and also carrying a similar catalytic material for promoting combustion reactions, said first electrical resistance element electrically isolated from said second electrical resistance element;

(d) a first pair of electrical elads operatively connected to said first resistance element;

(e) a first AC voltage power circuit coupled to the first pair of leads and operable to intermittently heat the first pair of leads ard operable to intermittently heat the first resistance element sufficient to cause substantial oxidatoin of the organic fluids passing by said first resistance element, and to produce a synchronous signal;

(f) a second pair of electrical leads operatively connected to said second resistance element for sensing variations in the electrical resistance thereof caused by temperature changes occurring from partial combustion at said second resistance element, said electrical resistance thereof represented by a second output electrical signal;

(g) a second voltage control circuit coupled to the second pair of elads being operable to heat and to maintain a temperature in the second resistance element that will promote substantially complete oxidation of the remaining organic fluid mixture impinging on said second resistance element; and (h) measuring circuit means adapted to be operatively joined to said first and said second pairs of leads being activated by and for processing the synchronous signal and the second output signal respectively whereby variations in the differential resistance of the second resistance element serve as a measure of the concentration of the organic fluid in the fluid mixture.

3. A detection instrument as set forth in claim 2, wherein the second resistance element comprises materials selected from Group VIII of the Periodic Table.

4. A detection instrument as set forth in claim 2, wherein the first voltage power circuit is actuated for on and off intervals of substantial equal duration with that duration, being a function of the mass of filament and both the thermal conductivity and the flow rate of the fluid mixture.

5. A detection instrument as set forth in claim 2, wherein the output signal of the measuring circuit is AC-coupled through a capacitor means and a resistor means, with both serving as a high pass filter, and producing a modified AC second output signal.

6. A detection instrument as set forth in claim 2 wherein the synchronous signal is representative of the frequency and phase of the output signal to be measured.

7. A detection instrument as set forth in claim 2, wherein the measuring circuit includes a lock-in amplification means comprising a synchronous modulator coupled with a low pass filter means which produces an improved output signal representative of the initial organic fluid concentration entering the detector.

8. A detection instrument as set forth in claim 2, wherein the first resistance element includes one or more materials selected from Group VIII of the Periodic Table.

9. A detection instrument as set forth in claim 8 where the Group VIII materials are selected from one or more of platinum, rhodium, ruthenium, and palladium.

10. A detection instrument as set forth in claim 2, wherein the second resistance element comprises a metal filament which functions as both a heater and as a thermal detector.

11. A detection instrument as set forth in claim 10, wherein the second output signal is passed to a combined amplifier and a second filter means, which condition said signal and produce a further modified third output signal for display on a metering means.

12. A detection instrument as set forth in claim 10, wherein the metal filament is platinum and the catalytic material is palladium for both of the first and second electrical resistance elements.

* * * * *